_United States Patent_ [19]

Macchio et al.

[11] Patent Number: 4,988,503

[45] Date of Patent: Jan. 29, 1991

[54] OIL-IN-WATER EMULSIONS FOR FOUNDATION MAKEUP COMPOSITION

[75] Inventors: Ralph A. Macchio, Monsey; Brent Slobody, New City, both of N.Y.; Julio G. Russ, Germantown, Tenn.

[73] Assignee: Revlon, Inc., New York, N.Y.

[21] Appl. No.: 469,156

[22] Filed: Jan. 24, 1990

[51] Int. Cl.$^5$ .............. D61K 7/021; D61K 7/480
[52] U.S. Cl. .................... 424/63; 424/69; 514/772; 514/844; 514/845
[58] Field of Search ............... 424/63, 69, 78; 514/772, 844, 845

[56] References Cited

U.S. PATENT DOCUMENTS

| | | | |
|---|---|---|---|
| 3,953,591 | 4/1976 | Snyder | 424/80 |
| 4,054,670 | 10/1977 | Buhler | 514/772 |
| 4,246,257 | 1/1981 | Elliott et al. | 424/78 |
| 4,303,676 | 12/1981 | Balazs | 514/773 |
| 4,342,742 | 8/1982 | Sebag et al. | 424/59 |
| 4,355,046 | 10/1982 | Suess | 514/772 |
| 4,423,041 | 12/1983 | Clum et al. | 514/772 |
| 4,500,676 | 2/1985 | Balazs et al. | 525/54.2 |
| 4,563,346 | 1/1986 | Deckner | 424/59 |
| 4,578,266 | 3/1986 | Tietjen et al. | 424/63 |
| 4,629,623 | 12/1986 | Balazas et al. | 424/63 X |
| 4,699,780 | 10/1987 | Jennings et al. | 424/60 |
| 4,784,844 | 11/1988 | Thimineur et al. | 424/65 |
| 4,801,447 | 1/1989 | Gum | 424/68 |
| 4,844,888 | 7/1989 | Zawadzki | 424/69 |
| 4,877,604 | 10/1989 | Schlossman | 424/64 |
| 4,919,922 | 4/1990 | Miyoshi et al. | 424/63 |

_Primary Examiner_—Thurman K. Page
_Assistant Examiner_—Susan S. Rucker

[57] ABSTRACT

A cosmetic foundation makeup composition comprising a liquid oil-in-water emulsion which comprises, in weight %, (a) about 0.1 to 15% of particulate talc,
(b) about 0.1 to 15% of particulate nylon,
(c) about 0.1 to 15% of a high molecular weight silicone oil,
(d) about 0.1 to 20% of a low molecular weight silicone oil,
(e) about 0.1 to 5% of sodium hyaluronate, and
(f) the balance, to 100%, of water.

12 Claims, No Drawings

OIL-IN-WATER EMULSIONS FOR FOUNDATION MAKEUP COMPOSITION

BACKGROUND OF THE INVENTION

1. Field of the Invention

This invention relates to an oil-in-water emulsion useful as a foundation makeup cosmetic composition. The composition contains at least 10% of non-polar silicone oil to give the product an emollient smooth finish when the emulsion is applied to the skin.

2. Prior Art

The traditional oil-in-water emulsions used as a foundation makeup cosmetic have never used high amounts of non-polar silicone oils (above 10%) since this leaves a wet or greasy film on the skin when applied. Moisturizing lotions or night creams have in the past used higher levels of oil since this is not a drawback in these products. Representative of this art is U.S. Pat. No. 4,246,257 which shows a moisturizing cream employing high levels of silicone oils (up to 30%) in combination with spherical particles (3-10%) of a polymer such as polyethylene, polystyrene or polymethyl- methacrylate having an average particle size of 5-15 microns, and preferably 5-7 microns. However, this cream is not used as a foundation.

It would be desirable to produce a foundation having the exceptional spreadability of a night cream without the greasy or wet feel associated with such creams.

It is an object of this invention to produce an oil-in-water emulsion having a relatively high level of non-polar silicone oil without the greasy feel associated with high oil containing emulsions.

SUMMARY OF THE INVENTION

This objective is achieved by using at least 10% by weight of a unique blend of silicone oils in combination with talc, nylon and sodium hyaluronate.

The liquid oil-in-water emulsion comprises, in weight %, (a) about 0.1 to 15%, and preferably about 3 to 7%, of particulate talc, (b) about 0.1 to 15%, and preferably about 1 to 3%, of particulate nylon, (c) about 0.1 to 15%, and preferably about 4 to 6%, of high molecular weight silicone oil, (d) about 0.1 to 20%, and preferably about 4.5 to 6.5%, of low molecular weight silicone oil, (e) about 0.1 to 5%, and preferably about 0.5 to 1.5%, of sodium hyaluronate, and (f) the balance, to 100%, of water.

DETAILED DESCRIPTION OF THE INVENTION

The talc and nylon components are both preferably used in the form of particles having an average particle size of less than about 10 microns and preferably of about 5 to 7 microns. The talc particles may also be treated with a thermoplastic polymer such as a polyolefin polymer such as polyethylene.

By being treated with the thermoplastic polymer, it is meant that the talc particles are coated with the thermoplastic polymer to the extent that the thermoplastic polymer comprises about 1 to 3 weight % of the coated talc.

The thermoplastic polymer provides a low surface energy polymer coating for the talc which increases the compatibility of the talc filler with the emollient oil phase of the emulsion.

The nylon component may be titanated and/or treated with thermoplastic resin. When titanated, the nylon particles are coated with a titanating agent such as isopropyl triisostearoyl titanate and other conventional titanating agents to the extent that the titanating agent comprises about 1 to 3 weight % of the titanated nylon. When treated or coated with the thermoplastic polymer, the nylon particles contain about 1 to 3% of the thermoplastic polymer.

Where the nylon is both titanated and treated with the thermoplastic polymer, the nylon particles can be titanated before or after being treated with the thermoplastic polymer.

The nylon spheres lower the surface energy of the film of the emulsion when the emulsion is applied to the skin and thus helps to provide for excellent spreading of the emulsion film over the skin.

The high molecular weight silicone oil component provides excellent slip properties to the emulsion, without any feel of greasiness or occlusivity. This oil also contributes to a cushioned feel provided by the emulsion. This solution of ultra high viscosity dimethiconol in a volatile cyclomethicone has a composite viscosity of about 5,000 to 10,000 cs at 25°±5° C. The high molecular weight silicone oil would include cyclomethicone/dimethiconol oil and other similar silicone oils as described in *CTFA Cosmetic Ingredient Dictionary*, Third Edition, published 1982 by the Cosmetic, Toiletry and Fragrance Association, Inc., Washington, D.C.

The low molecular weight silicone oil component increases the silicone oil content of the emulsion to levels not previously realized, it is believed, for traditional silicone oil-in-water cosmetic emulsion systems. The use of the low molecular weight silicone oil provides for exceptional spreadability of the emulsion and helps to provide an elegant soft feel on the skin. The low molecular weight silicone oil has a viscosity of about 5 to 500 cs at 25°± 5° C. The low molecular weight silicone oils include methylated linear siloxane polymers (CFTA name dimethicone).

The sodium hyaluronate is employed as a moisturizing agent. It is usually added to the emulsion system in the form of a 1% by weight solution in water. This high molecular weight hygroscopic material contributes to the viscous flow gravity of the foundation product. It also forms a non-tacking transparent film which is exceptionally smooth.

The resulting product can be used per se as a cosmetic which is applied to soothe and moisturize the skin. One can also add optional ingredients such as cosmetically acceptable fillers, pigments, and/or fragrance. As is well recognized in this field, many materials can serve simultaneously as fillers, to add body to the product, and as colorants, to make the product white or a shade such as red. Examples of fillers are talc, mica, silica, kaolin, magnesium silicate, magnesium carbonate, calcium silicate, calcium carbonate, powdered nylon, and combinations thereof. Examples of colorants include iron oxide, titanium dioxide, talc, mica, ultramarine, bismuth oxychloride, chromium oxides, chromium hydroxide, carmine, manganese violet, ferric ferrocyanide, FDA certified organic dyes and lakes, metallic powders, and equivalents. The total of fillers plus colorants can comprise up to 30% by weight of the product of this invention. The cosmetic formulator will recognize that a blend of fragrance oils such as is conventionally supplied by fragrance manufacturers can be added, in amounts generally ranging up to about 0.5 weight %. As preservatives one can use methyl or propyl paraben or their equivalent in amounts up to about 1%. The composition can contain up to 10% by weight and preferably about 5% of one or more cosmetically acceptable oils to further augment the feel of the product on the skin and to adjust the product's consistency. Suitable oils include glycerol diesters and $C_{10}$–$C_{22}$ alcohol esters of $C_{10}$–$C_{22}$ fatty acids. The ordinarily skilled formulator will recognize that other compounds known to be equivalent to those listed herein can be incorporated into the composition of this invention.

The emulsion systems of the present invention also contain one or more of the following optional components, in weight %, about 0.1 to 5%, and preferably of about 3%, of one or more emulsifying agents. Such emulsifying agents would include sorbitan sesquioleate, polyethylene glycol ethers of stearyl alcohol, and others conventional emulsifiers, about 0.01 to 15%, and preferably about 8%, of one or more alcohols such as propylene glycol, about 0.1 to 2%, and preferably about 0.2%, of one or more gums such as carboxymethyl cellulose, xanthan gum, magnesium aluminum silicate, etc., and about 0.01 to 2%, and preferably about 0.1%, of one or more chelating agents such as trisodium EDTA.

In the Example, the dry ingredients (preservatives, fillers, colors) are mixed into the liquid using high sheer equipment. When the resulting mixture was homogenous and uniformly dispersed, the mixture was heated to 75° C. In a separate container, all oils (both organic esters and silicone compounds) are mixed and heated to 75° C. This phase is subsequently poured into the previously milled water phase for emulsification. The composition is mixed and cooled to room temperature before being poured into its intended package. No phase separation occurred during or after cooling of the product. All solid ingredients, including water, talc and nylon, were added in finely divided form.

EXAMPLE

An oil-in-water emulsion of the present invention was prepared from the following formulation, in kilograms.

| Component | Weight of Component, kg |
| --- | --- |
| Water | 46.48 |
| Propylene glycol | 8.00 |
| Carboxymethylcellulose | 0.10 |
| Magnesium aluminum silicate | 0.40 |
| Xanthan gum | 0.20 |
| Triethanolamine | 1.50 |
| Ceteth 10 | 1.00 |
| Methyl paraben | 0.25 |
| Trisodium EDTA | 0.05 |
| Quaternium 15 | 0.10 |
| Sorbitan sesquioleate | 0.20 |
| Talc treated with 1.5% PE | 1.00 |
| Nylon, titanated and treated with 1% PE | 2.00 |
| Silica | 0.10 |
| Iron Oxides/Talc | 14.00 |
| Stearic acid | 2.00 |
| Isostearic acid | 1.00 |
| Dimethicone (5–500 cs) | 14.50 |
| Steareth 2 | 0.75 |
| Propyl paraben | 0.10 |

| Component | Weight of Component, kg |
| --- | --- |
| Propylene glycol dicaprylate/dicaprate | 2.00 |
| Isocetyl stearate | 2.00 |
| Octyl methoxy cinnamate | 2.00 |
| Cyclomethicone/dimethiconol (5,000–10,000 cs) | 5.00 |
| Perfume oil | 0.10 |
| Mineral salts | 0.02 |
| Mucopolysaccharides | 0.05 |
| Adenosine triphosphate | 0.10 |
| Sodium hyaluronate, as 1% aqueous solution | 1.00 |
| | 100.00 |

Steareth 2, Ceteth 10, and Quaternium 15 are all described in the CFTA Handbook. Steareth 2 and Ceteth 10 are surfactants and are polymethyl glycols of stearyl alcohol and cetyl alcohol respectively. Quaternium 15 is a quaternary ammonium compound which acts as a preservative.

When the emulsion is applied to the skin as a foundation makeup, it spreads easily and extensively over the skin and provides a smooth finish and a cushioned soft feel.

What is claimed is:

1. A cosmetic foundation makeup composition comprising an oil-in-water emulsion which comprises, in weight %,
    (a) about 0.1 to 15% of particulate talc,
    (b) about 0.1 to 15% of particulate nylon,
    (c) about 0.1 to 15% of a silicone oil having a viscosity of 5,000 to 10,000 cs,
    (d) about 0.1 to 20% of a silicone oil having a viscosity of 5 to 500 cs,
    (e) about 1 to 5% of sodium hyaluronate, and
    (f) the balance, to 100%, of water.

2. A cosmetic composition as in claim 1 in which said (a) and (b) components have an average particle size of less than 10 microns.

3. A cosmetic composition as in claim 1 in which said (a) component is treated with polyethylene.

4. A composition as in claim 1 in which said (b) component is titanated and treated with polyethylene.

5. A composition as in claim 1 in which said (c) component comprises cyclomethicone/dimethiconol fluid.

6. A composition as in claim 1 in which said (d) component comprises dimethicone.

7. A cosmetic foundation makeup composition comprising an oil-in-water emulsion which comprises, in weight %,
    (a) about 3 to 7% of particulate talc,
    (b) about 1 to 3% of particulate nylon,
    (c) about 4 to 6% of a silicone oil having a viscosity of 5,000 to 10,000 cs,
    (d) about 4.5 to 6.5% of a silicone oil having a viscosity of 5 to 500 cs,
    (e) about 0.5 to 1.5% of sodium hyaluronate, and
    (f) the balance, to 100%, of water.

8. A cosmetic composition as in claim 7 in which said (a) and (b) components have an average particle size of less than 10 microns.

9. A cosmetic composition as in claim 7 in which said (a) component is treated with polyethylene.

10. A composition as in claim 7 in which said (b) component is titanated and treated with polyethylene.

11. A composition as in claim 7 in which said (c) component comprises cyclomethicone/dimethiconol fluid.

12. A composition as in claim 7 in which said (d) component comprises dimethicone.

* * * * *